United States Patent
Huang

(10) Patent No.: US 8,195,005 B2
(45) Date of Patent: Jun. 5, 2012

(54) IMAGE PROCESSING, IMAGE FEATURE EXTRACTION AND IMAGE MATCHING APPARATUSES, METHODS AND PROGRAMS, AND IMAGE MATCHING SYSTEM

(75) Inventor: Lei Huang, Tokyo (JP)

(73) Assignee: NEC Corporation, Tokyo (JP)

( * ) Notice: Subject to any disclaimer, the term of this patent is extended or adjusted under 35 U.S.C. 154(b) by 975 days.

(21) Appl. No.: 12/223,390

(22) PCT Filed: Feb. 1, 2007

(86) PCT No.: PCT/JP2007/051692
§ 371 (c)(1),
(2), (4) Date: Jul. 30, 2008

(87) PCT Pub. No.: WO2007/088926
PCT Pub. Date: Aug. 9, 2007

(65) Prior Publication Data
US 2009/0022401 A1    Jan. 22, 2009

(30) Foreign Application Priority Data
Feb. 1, 2006   (JP) .................................. 2006-024636

(51) Int. Cl.
*G06K 9/32* (2006.01)
*G06K 9/46* (2006.01)
*A63F 9/24* (2006.01)

(52) U.S. Cl. ........................... 382/284; 382/190; 463/29

(58) Field of Classification Search .................. 382/115, 382/124, 173, 190, 209, 218, 219, 254, 274, 382/305, 312, 284; 358/1.1; 463/1, 29; 715/788, 715/798
See application file for complete search history.

(56) References Cited

U.S. PATENT DOCUMENTS

| | | | | |
|---|---|---|---|---|
| 7,072,523 B2 * | 7/2006 | Bolle et al. | ..................... | 382/254 |
| 7,076,099 B2 * | 7/2006 | Kondo et al. | ................. | 382/203 |
| 7,388,970 B2 * | 6/2008 | Mihara et al. | ................. | 382/107 |
| 7,680,305 B2 * | 3/2010 | Miura et al. | ................. | 382/115 |

FOREIGN PATENT DOCUMENTS

| | | |
|---|---|---|
| JP | 2-293981 | 12/1990 |
| JP | 4-322382 | 11/1992 |
| JP | 8-110945 | 4/1996 |
| JP | 9-167230 | 6/1997 |

(Continued)

*Primary Examiner* — Kanjibhai Patel
(74) *Attorney, Agent, or Firm* — McGinn IP Law Group, PLLC

(57) ABSTRACT

An object of the present invention is to eliminate instability in processing results of either one of image restoration processing, image feature extraction processing, and image matching processing, which is caused depending on an image division method, to enhance identification accuracy in image matching. An image processing apparatus includes an image input section, a data processing section, and a result output section. The data processing section includes a controller, an image-dividing-method dictionary, an image division section, an image processing section and an image integration section. The image division section divides image data into a plurality of regions according to a plurality of image dividing methods set in advance in the image-dividing-method dictionary. The image processing section processes the image data divided according to the image dividing methods by the image division section and generates a plurality of restored image data. The image integration section generates integrated image data of the entire image by using the plurality of the restored image data obtained from the processing that the image division section and image processing section perform according to the plurality of the image division methods.

9 Claims, 10 Drawing Sheets

FOREIGN PATENT DOCUMENTS

| | | |
|---|---|---|
| JP | 2000-259825 | 9/2000 |
| JP | 2001-266154 | 9/2001 |
| JP | 2002-99912 | 4/2002 |
| JP | 2004-192603 | 7/2004 |
| JP | 2005-115548 | 4/2005 |
| JP | 2005-141453 | 6/2005 |

* cited by examiner

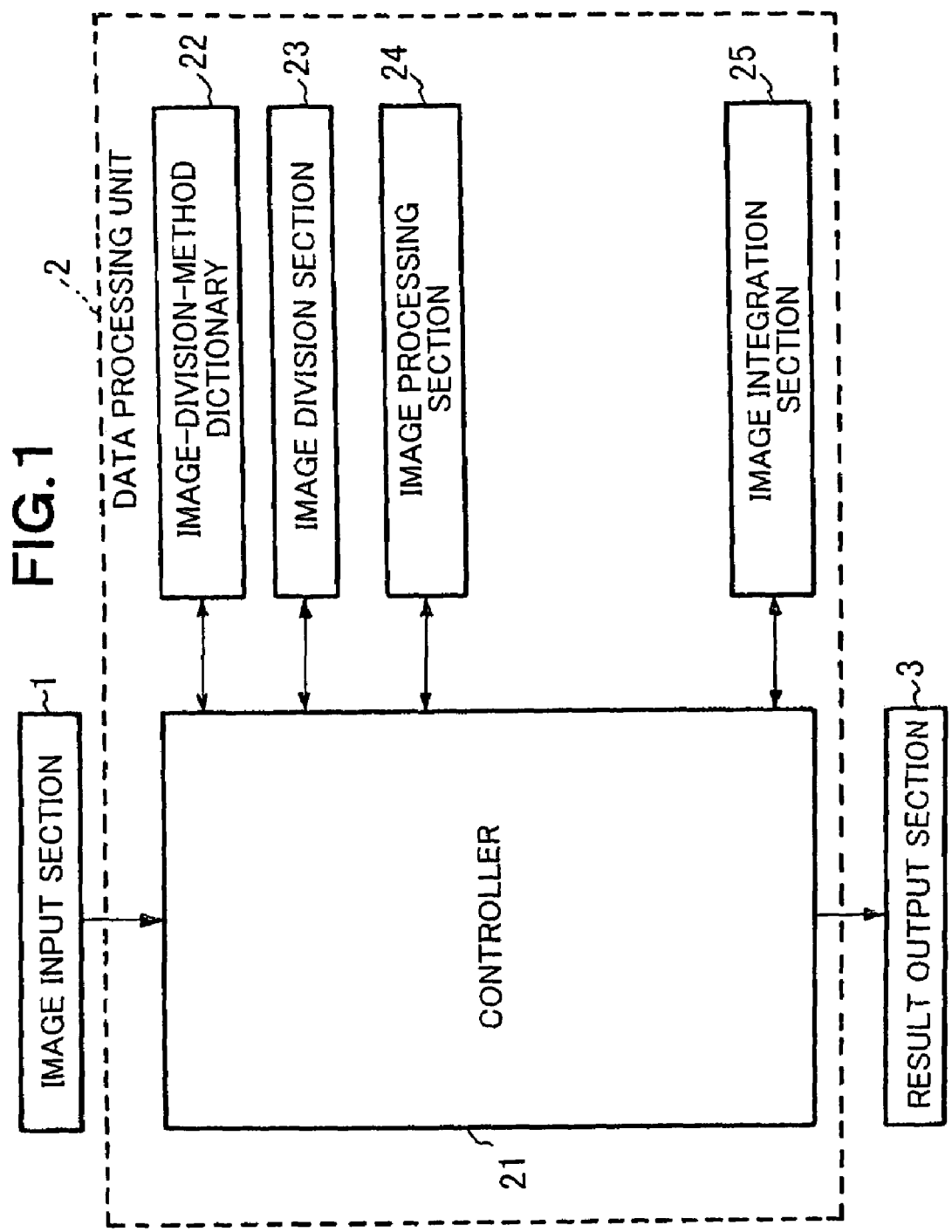

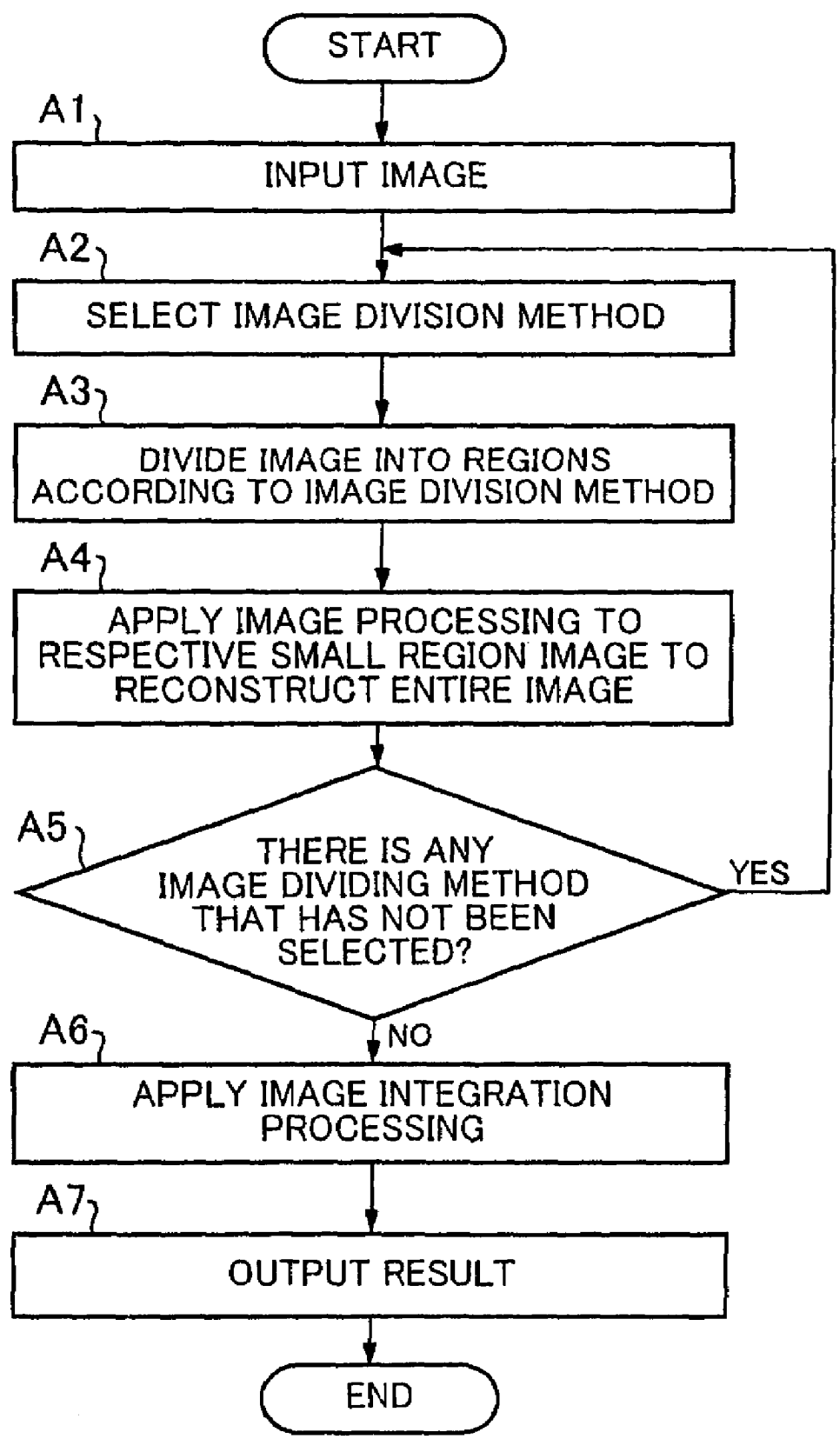

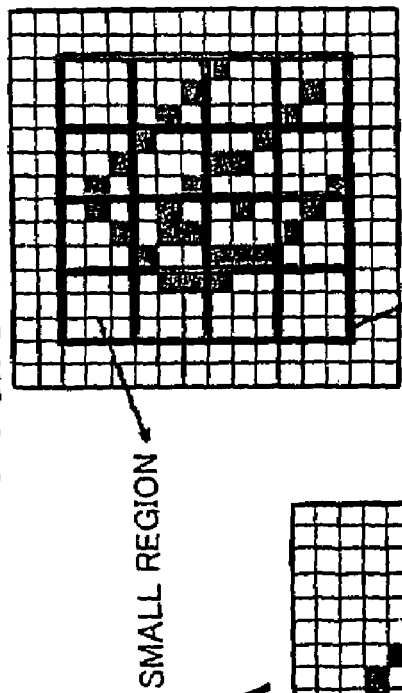
FIG.3B — SMALL REGION — IMAGE DIVISION METHOD 1
FIG.3C — IMAGE DIVISION METHOD 2
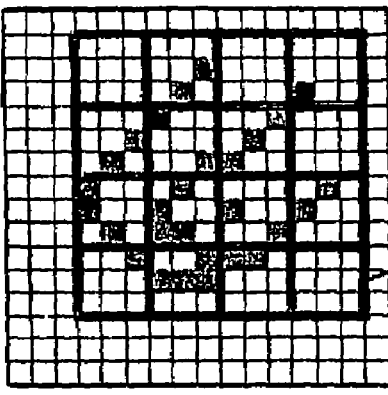
FIG.3E — IMAGE DIVISION METHOD 4
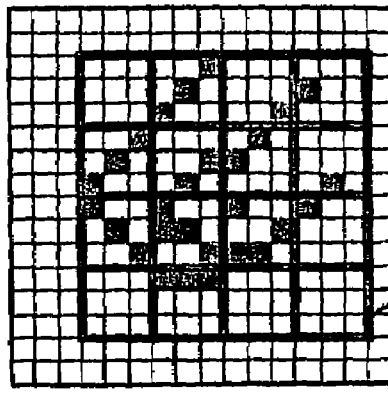
FIG.3D — IMAGE DIVISION METHOD 3
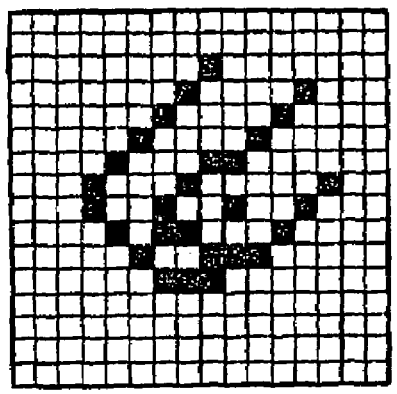
FIG.3A — FINGERPRINT IMAGE

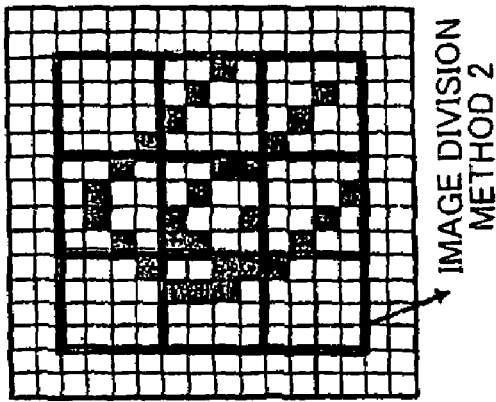
FIG.4C IMAGE DIVISION METHOD 2
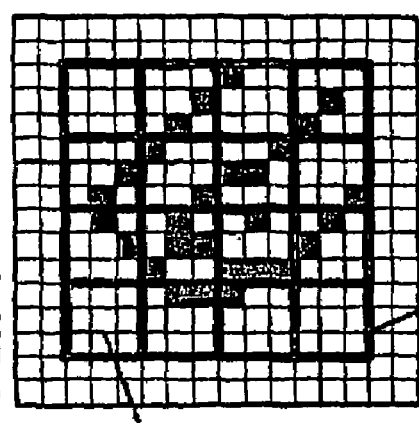
FIG.4B IMAGE DIVISION METHOD 1
SMALL REGION
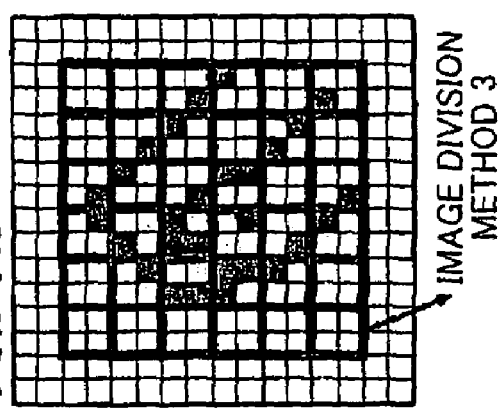
FIG.4D IMAGE DIVISION METHOD 3
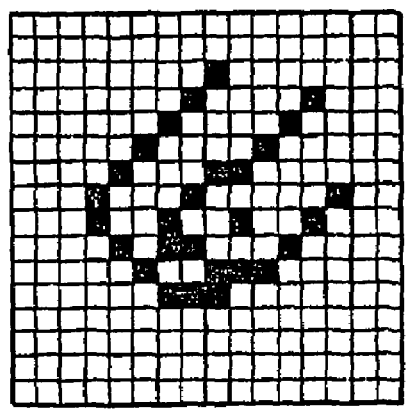
FIG.4A FINGERPRINT IMAGE

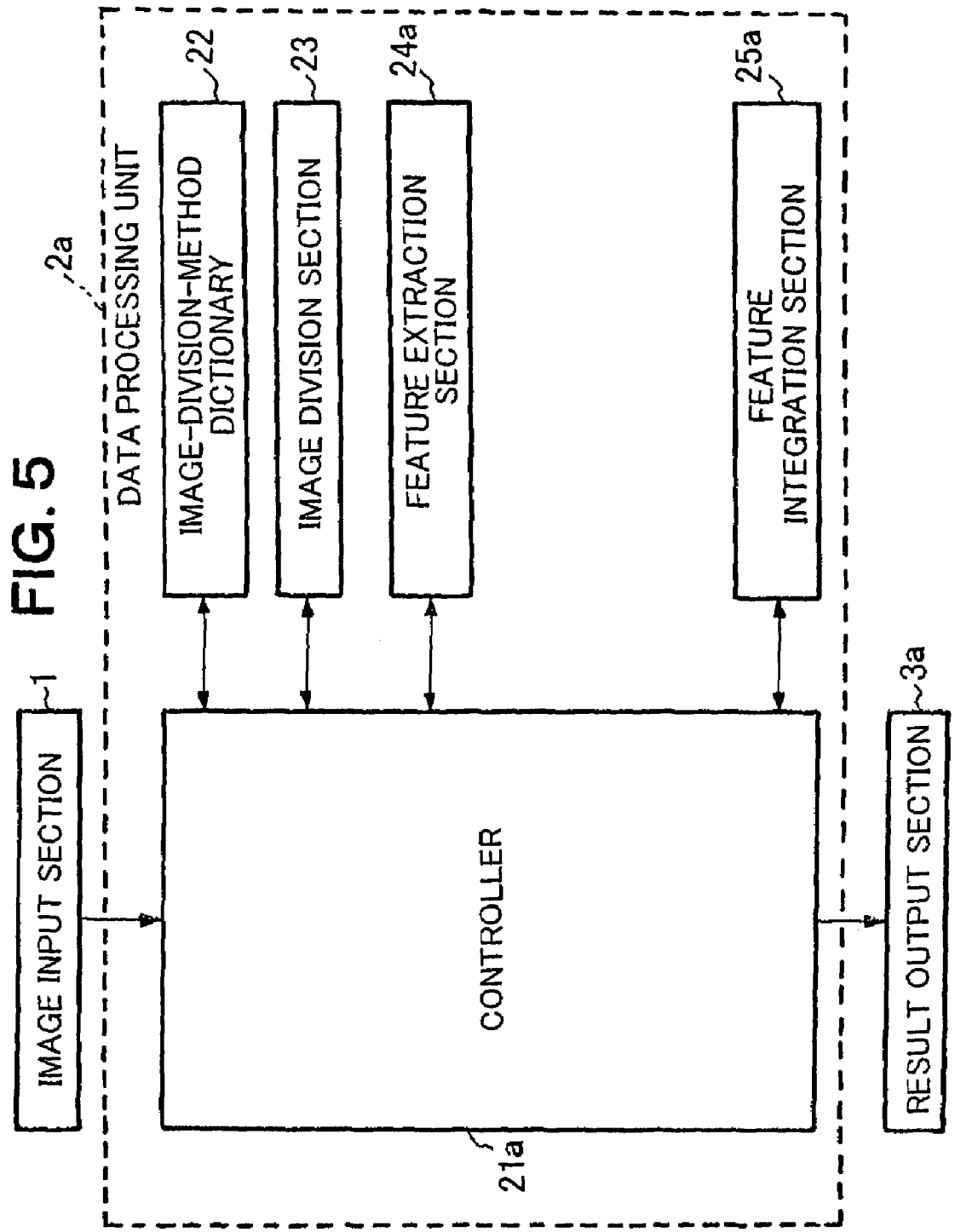

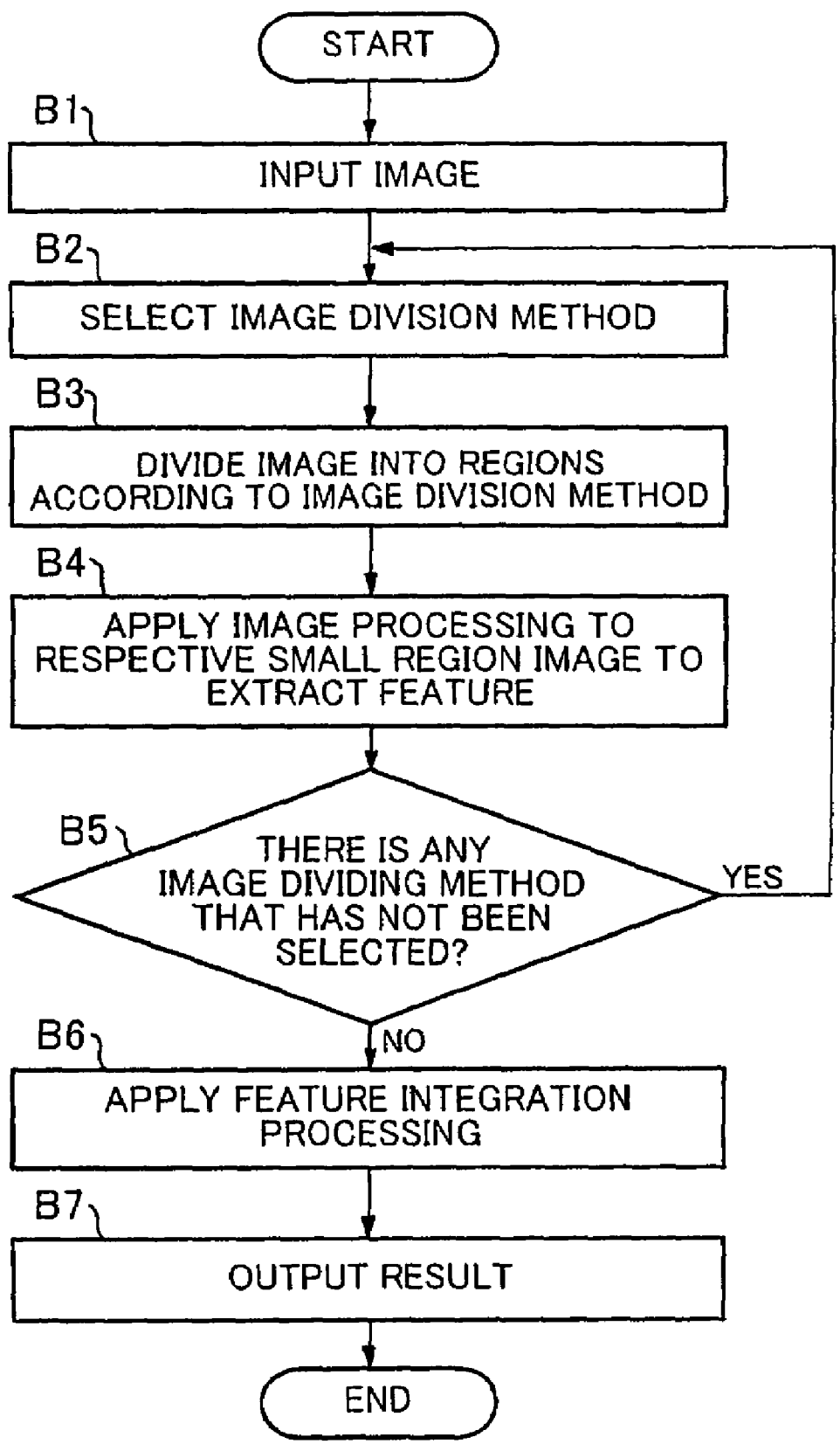

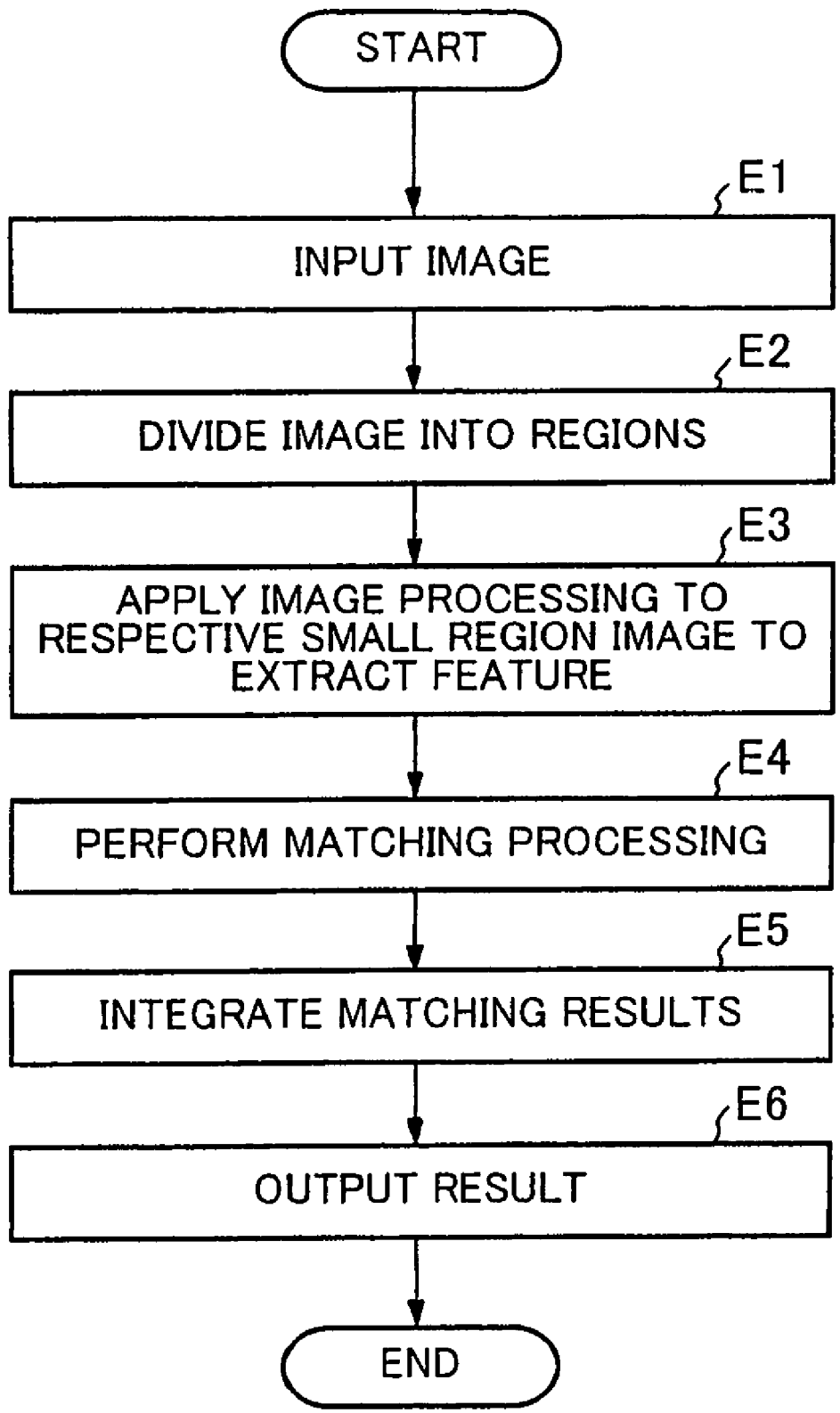

IMAGE PROCESSING, IMAGE FEATURE EXTRACTION AND IMAGE MATCHING APPARATUSES, METHODS AND PROGRAMS, AND IMAGE MATCHING SYSTEM

TECHNICAL FIELD

The present invention relates to image processing, image feature extraction, and image matching apparatuses, methods and programs, and an image matching system and, more particularly, to image processing, image feature extraction, and image matching techniques suitably used for processing a fingerprint pattern image, a palm pattern image, a muzzle pattern image, an iris pattern image, a face pattern image, a vein pattern image, and a texture pattern image.

BACKGROUND ART

There is known an image processing technique for removing noise from an image or emphasizing an image which has been used in an apparatus for displaying an image or used as pre-processing for image feature extracting processing/image matching processing. An example of an image processing apparatus using this technique is disclosed in Patent Document 1.

This conventional image processing apparatus includes a block splitting section, a Fourier transform section, a maximum amplitude frequency search section, a noise power reducing section, an inverse Fourier transform section, and an image reconstruction section. The block splitting section splits an input image into a plurality of blocks. The Fourier transform section applies discrete Fourier transform to the obtained images of the respective blocks. The maximum amplitude frequency search section searches for a frequency giving a maximum amplitude from the obtained Fourier component information. The noise power reducing section sets a gain at each frequency so that a value for the gain is reduced gradually when a frequency is separated further from a frequency giving the maximum amplitude and multiplies the gain by the obtained Fourier component information. The inverse Fourier transform section applies inverse Fourier transform to the Fourier component with the changed amplitude. The image reconstruction section combines the transformed images of the respective blocks together so as to reconstruct the entire image after restoration.

The conventional image processing apparatus having the configuration described above operates as follows: applies Fourier transform to an images for each fine block; finds a frequency component giving a maximum amplitude for each block; estimates the found frequency component as a main stripe pattern in each block; and perform processing such that the value of a frequency component decreases as the frequency component is separated from the frequency giving the maximum amplitude, thereby emphasizing ridges while reducing noise.

Patent Document 1: JP 2005-115548A (pages 4 to 5, FIG. 2)

DISCLOSURE OF THE INVENTION

Problems to be Solved by the Invention

However, the following problems exist in the conventional image processing apparatus.

The first problem is that uncertain image processing results are likely to be obtained. The reason is as follows. The interval between stripes constituting a fingerprint pattern varies between individuals, and the stripes are arranged in various patterns in one image. Thus, in a conventional technique in which stripes are locally approximated with two-dimensional sine waves, when the size of the local region in which stripes are locally approximated is set larger, it becomes increasingly likely that ridge lines of various directions are included in a portion at which the interval between the stripes is small, which may degrade the restoration accuracy of a small region image; while when the size of the local region is set smaller in order to avoid the above problem, the restoration accuracy of an image in a portion at which the interval between the stripes is large may be degraded.

The second problem is that uncertain structure patterns or uncertain feature point information are likely to be extracted from an image. This is because that results of image digitization, results of extraction of structure patterns, or results of extraction of feature points depend on results of image restoration processing such as image noise removal.

The third problem is that uncertain matching results between images are likely to be obtained. This is because that the matching results between images depend on structure patterns or feature point information extracted from images.

The fourth problem is that the identification accuracy of an image matching system is degraded. This is because that the matching score between images obtained in the image matching system depends on a matching result between images and, therefore, uncertainty of the matching scores between images may increase an identification error rate in the image matching system.

The present invention has been made in view of the above circumstances, and an object thereof is to eliminate instability in processing results of either one of image restoration processing, image feature extraction processing, and image matching processing, which is caused depending on an image division method, to enhance identification accuracy in image matching.

Means for Solving the Problems

To achieve the above object, an image processing apparatus according to the present invention is characterized by comprising: an image enhancement means for enhancing an input image for each division region; a control means for causing the image enhancement means to act on the input image according to a plurality of input image division methods; and an image integration means for integrating the input images enhanced using the plurality of input image division methods into one integrated image.

In the present invention, the image enhancement means may perform preprocessing for extracting the feature of the input image. The image enhancement means may remove noise from the input image. The image integration means may set the average value of pixel values of a given pixel located at the same position in the respective input images enhanced using the plurality of input image division methods as the value of a pixel at the same position in the integrated image.

An image feature extraction apparatus according to the present invention is characterized by comprising: an image feature extraction means for dividing an input image into a plurality of regions and extracting an image feature from each region; a control means for causing the image feature extraction means to act on the input image according to a plurality of input image division methods; and an image feature output means for outputting a plurality of feature data extracted using the plurality of input image division methods.

In the present invention, the image feature extraction apparatus may further comprise a feature integration means for generating integrated feature data of the entire input image by using the plurality of feature data. The feature integration means may set the average value of corresponding feature amounts of the plurality of the feature data as the feature amount of the integrated feature data.

An image matching apparatus according to the present invention is characterized by comprising: a matching means for dividing an input image into a plurality of regions, extracting an image feature from each region, performing matching between the image feature and feature data for authentication so as to generate a matching result; a control means for causing the image matching means to act on the input image according to a plurality of input image division methods; and a matching integration means for integrating a plurality of matching results obtained using the plurality of input image division methods to generate integrated matching data.

In the present invention, the matching integration means may set common corresponding feature amount of the plurality of matching data as the corresponding feature amount of the integrated matching data.

In the above apparatuses, at least one of the position, size, and shape of the division region may be different between the plurality of input image division method.

An image processing method according to the present invention is characterized by comprising the steps of: applying processing to image data while changing a previously set image division method to obtain a plurality of processed image data; and generating integrated image data using the plurality of processed image data.

An image feature extraction method according to the present invention is characterized by comprising the steps of: obtaining a plurality of feature data from image data by changing a previously set image division method; and generating integrated feature data using the plurality of feature data.

An image matching method according to the present invention is characterized by comprising the steps of: obtaining a plurality of feature data from image data by changing a previously set image division method; and performing matching between the plurality of feature data and externally input feature data for authentication to obtain a plurality of matching data; and generating integrated matching data using the plurality of matching data.

In the above methods, the step of obtaining the plurality of processed image data may change at least one of the position, size, and shape of an image division region to change the image division method.

An image matching system according to the present invention is characterized by comprising: a means for obtaining a plurality of feature data from image data by changing a previously set image division method; a means for performing matching between the plurality of feature data and externally input feature data for authentication to obtain a plurality of matching score data; a means for generating integrated matching score data using the plurality of matching score data; and a means for comparing the integrated matching score data and a previously set threshold to perform authentication.

In the present invention, the step of obtaining the plurality of feature data may change at least one of the position, size, and shape of an image division region to change the image division method. Further, the means for generating the integrated matching score data calculates at least one of the average value, maximum value, and minimum value of the plurality of matching score data to set the calculated value as the value of the integrated matching score data.

An image processing program according to the present invention is characterized by allowing a computer to execute the steps of: applying processing to image data while changing a previously set image division method to obtain a plurality of processed image data; and generating integrated image data using the plurality of processed image data.

An image feature extraction program according to the present invention is characterized by allowing a computer to execute the steps of: obtaining a plurality of feature data from image data by changing a previously set image division method; and generating integrated feature data using the plurality of feature data.

An image matching program according to the present invention is characterized by allowing a computer to execute the steps of: obtaining a plurality of feature data from image data by changing a previously set image division method; performing matching between the plurality of feature data and externally input feature data for authentication to obtain a plurality of matching data; and generating integrated matching data using the plurality of matching data.

Advantages of the Invention

According to the present invention, it is possible to eliminate instability in processing results of either one of image restoration processing, image feature extraction processing, and image matching processing, which is caused depending on an image division method, to enhance identification accuracy in image matching.

BRIEF DESCRIPTION OF THE DRAWINGS

FIG. 1 is a block diagram showing a configuration of an image processing apparatus according to a first exemplary embodiment of the present invention;

FIG. 2 is a flowchart showing operation of the image processing apparatus according to the first exemplary embodiment of the present invention;

FIGS. 3A to 3E are views showing concrete examples of image division methods;

FIGS. 4A to 4D are views showing other concrete example of the image division methods;

FIG. 5 is a block diagram showing a configuration of an image feature extraction apparatus according to a second exemplary embodiment of the present invention;

FIG. 6 is a block diagram showing operation of an image feature extraction apparatus according to the second exemplary embodiment of the present invention;

FIG. 10 is a flowchart showing operation of the image matching apparatus according to a fourth exemplary embodiment of the present invention at matching time.

EXPLANATION OF REFERENCE SYMBOLS

Figure 7:
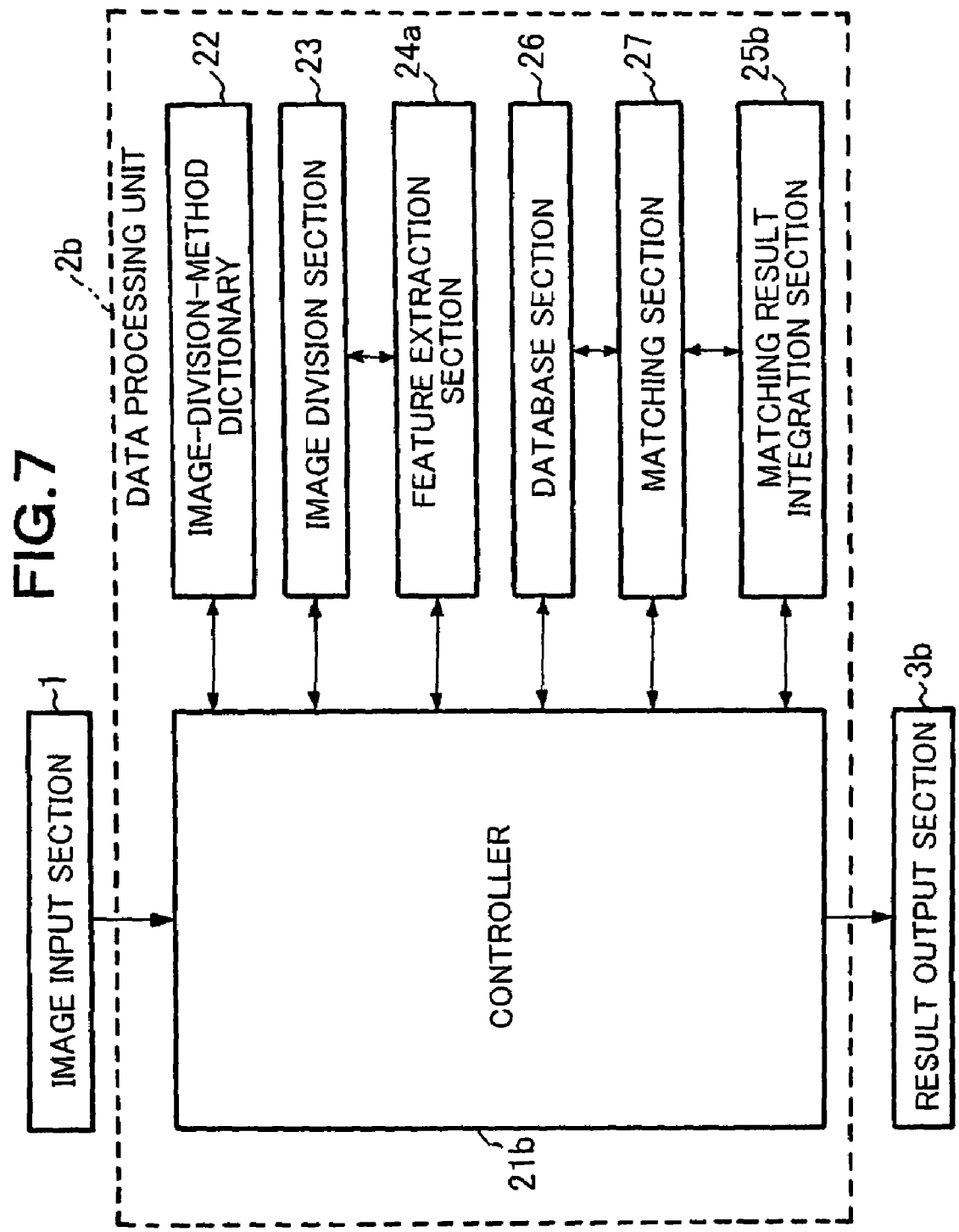
FIG. 7 is a block diagram showing a configuration of an image matching apparatus according to a third exemplary embodiment of the present invention.

1: Image input section
2, 2a, 2b: Data processing unit
3, 3a, 3b: Result output section
21, 21a, 21b: Controller 22: Image-division-method dictionary
23: Image division section
24: Image processing section
24a: Feature extraction section
25: Image integration section
25a: Feature integration section
25b: Matching result integration section
26: Database section
27: Matching section

DESCRIPTION OF EXEMPLARY EMBODIMENTS

Now, exemplary embodiments for practicing the present invention will be described in greater detail by referring to the accompanying drawings.

In the exemplary embodiments of the present invention, an image processing method or image feature extraction method applies image restoration processing or feature extraction processing to an image to be processed and displays a result of the processing on an output unit such as a display. Further, an image matching method or image matching system checks a matching between image data to be checked and image data or feature data stored in a database and displays the obtained matching result such as a matching score on an output unit such as a display or compares the matching result with a determination threshold to thereby perform identification determination.

Examples of the images to be processed by the above method and system include, e.g., a fingerprint pattern image, a palm pattern image, a muzzle pattern image, a face pattern image, an iris pattern image, and a vein pattern image of a person or an animal. The following description will be made using a fingerprint image as an example of an image to be processed. However, the present invention may be applicable not only to the fingerprint image but also any other types of image without departing from the scope of the present invention.

(First Exemplary Embodiment)

A first exemplary embodiment of the present invention will be described in detail with reference to FIGS. 1 to 4.

Referring to FIG. 1, an image processing apparatus according to the present exemplary embodiment includes an image input section 1 that holds and supplies a fingerprint image input through a fingerprint direct input device or the like, a data processing unit 2 that operates under program control, and a result output section 3 that outputs a processing result.

The data processing unit 2 functionally includes an image-division-method dictionary 22, an image division section 23, an image processing section 24, an image integration section 25, and a controller 21.

The above respective section roughly operate as follows. The image-division-method dictionary 22 stores a plurality of image division methods (to be described later) used for dividing a fingerprint image supplied from the image input section 1 into a plurality of small regions. The image division section 23 divides the fingerprint image supplied from the image input section 1 into a plurality of small regions according to the image division method specified by the image-division-method dictionary 22. The image processing section 24 processes image data of the fingerprint image divided by the image division section 23 for each small region to generate image restoration data. The image integration section 25 generates one integration image data from the image restoration data corresponding to the respective image division methods, which are generated by the image processing section 24. The controller 21 controls the above respective section in the data processing unit 2. The functions of the above section are realized by a computer executing a previously set program. This program is stored in a storage medium such as a memory or a hard disk.

With reference to FIG. 1 and a flowchart of FIG. 2, the entire operation of the present exemplary embodiment will be described in detail.

A fingerprint image input to the image input section 1 is supplied to the controller 21 (step A1 in FIG. 2). The controller 21 then searches the image-division-method dictionary 22 storing a plurality of image division methods, selects one image division method from image division methods that have not been selected, loads therein the selected one image division method, and supplies, to the image division section 23, the loaded image division method and fingerprint image supplied from the image input section 1 (step A2).

Examples of the plurality of image division methods include those shown in FIG. 3. In FIG. 3, FIG. 3A is a schematic view of the fingerprint image, and FIGS. 3B to 3E show examples in which different four types of block division methods are applied to the same fingerprint image. In either block division method, the entire region of the fingerprint image is divided in 4×4 blocks each having the same size. However, the starting positions of the blocks differ between all the division methods, differentiating all the block division methods from one another. Further, although the adjacent blocks do not overlap each other in these examples, a configuration may be employed in which the adjacent blocks may partially overlap each other, as disclosed in JP 2005-115548A. Further, the size or shape of each small region may be made different from those of examples shown in FIG. 3.

Other examples of the plurality of image division methods include those shown in FIG. 4. In FIG. 4, FIG. 4A is a schematic view of the fingerprint image, and FIGS. 4B to 4D show examples in which different three types of block division methods are applied to the same fingerprint image. In these examples, the block sizes of the respective block division methods are different from one another, differentiating all the block division methods from one another. While the position and size of the small regions are changed in examples of FIGS. 3 and 4, respectively, the shape of each small region is not limited to a rectangular shape as shown in FIGS. 3 and 4, but may be a polygonal shape such as a triangle, pentagon, or hexagon.

Then, the image division section 23 divides the fingerprint image into a plurality of small regions according to the image division method supplied from the controller 21 and supplies, to the image processing section 24, the obtained small region image data (step A3). Subsequently, the image processing section 24 applies image processing to the respective small region image data supplied from the controller 21 to reconstruct the entire image after restoration based on the processing results, and supplies the reconstructed image data to the controller 21 (step A4).

The image processing section 24 can be realized by a conventional technique. For example, JP 2005-115548A discloses a noise removal method including: transforming a plurality of block images obtained by a block splitting section into frequency components by discrete Fourier transform; searching for a frequency giving a maximum amplitude from the obtained Fourier component information; setting a gain at each frequency so that a value for the gain is reduced gradually when a frequency is separated further from a frequency giving the maximum amplitude; multiplying the gain by the obtained Fourier component information to reduce noise power; applying inverse Fourier transform to the Fourier component with the changed amplitude; combining the transformed images of the respective blocks together so as to construct the entire image after restoration.

Then, the controller 21 determines whether there exists any image division method that has not been loaded into the controller 21 among the image division methods stored in the image-division-method dictionary 22 (step A5). When determining that there exists any image division method that has not been loaded into the controller 21 (YES in step A5), the controller 21 repeatedly executes the processing from steps A2 to A4 until all the image division methods are loaded therein. On the other hand, when determining that there exists no image division method that has not been loaded into the controller 21 (NO in step A5), the controller 21 supplies, to the image integration section 25, image data corresponding to the respective image division methods which are processed by the image processing section 24.

Then, the image integration section 25 generates one integrated image data from a plurality of restored image data corresponding to respective image division methods supplied from the controller 21 and supplies, to the controller 21, the integrated image data as a processing result (step A6). In this image integration processing, the image integration section 25 uses the average value of pixel values of a given pixel located at the same position in the respective restored image data as a new pixel value for the plurality of restored image data processed by the image processing section 24 to construct the entire image data after integration.

Finally, the controller 21 supplies, to the result output section 3, the integrated image data supplied from the image integration section 25 (step A7). The output unit mentioned here may be a display unit such as a display in the usage where an operator checks the quality of a restored fingerprint image.

Therefore, according to the present exemplary embodiment, by previously storing a plurality of image division methods, processing input image data for respective image division methods, and generating one integrated image data from image processing results corresponding to the respective image division methods, instability in the image processing results, which is caused depending on the image division method, can be reduced to thereby provide stable image processing results.

Further, in the present exemplary embodiment, the position of the division region of the image is shifted to thereby change the image division method. Thus, it is possible to realize the image processing apparatus according to the present invention with a simple configuration.

(Second Exemplary Embodiment)

A second exemplary embodiment of the present invention will be described in detail with reference to FIGS. 5 and 6.

Referring to FIG. 5, an image feature extraction apparatus according to the present exemplary embodiment includes an image input section 1 that holds and supplies a fingerprint image input through a fingerprint direct input device or the like, a data processing unit 2a that operates under program control, and a result output section 3a that outputs a processing result.

The data processing unit 2a functionally includes an image-division-method dictionary 22, an image division section 23, a feature extraction section 24a, a feature integration section 25a, and a controller 21a.

The above respective section roughly operate as follows. The image-division-method dictionary 22 and image division section 23 operate in the same manner as in the first exemplary embodiment, and the descriptions thereof are omitted here. The feature extraction section 24a processes image data of the fingerprint image divided by the image division section 23 for each small region to extract a feature based on the processing result. The feature integration section 25a integrates feature data corresponding to respective image division methods which are extracted by the feature extraction section 24a. The controller 21a controls the above respective section in the data processing unit 2a. The functions of the above section are realized by a computer executing a previously set program. This program is stored in a storage medium such as a memory or a hard disk.

With reference to FIG. 5 and a flowchart of FIG. 6, the entire operation of the present exemplary embodiment will be described in detail.

A fingerprint image input to the image input section 1 is supplied to the controller 21a (step B1 in FIG. 5). The controller 21a then searches the image-division-method dictionary 22 storing a plurality of image division methods, selects one image division method from image division methods that have not been selected, loads therein the selected one image division method, and supplies, to the image division section 23, the loaded image division method and fingerprint image supplied from the image input section 1 (step B2). The plurality of image division methods are the same as those in the first exemplary embodiment (see the description related to step A2), and the description thereof is omitted here.

Then, the image division section 23 divides the fingerprint image into a plurality of small regions according to the image division method supplied from the controller 21a and supplies, to the feature extraction section 24a, the obtained small region image data (step B3). Subsequently, the feature extraction section 24a applies image processing to the respective small region image data supplied from the controller 21a to reconstruct the entire image based on the processing results, extracts a feature from the reconstructed restored image data, and supplies the extracted feature data to the controller 21a (step B4).

The image processing method and the image reconstruction method are the same as those in the first exemplary embodiment (see the description related to step A4), and the description thereof is omitted here. The method of extracting a feature from an image is realized by a conventional technique. For example, JP 60-012674B discloses a feature point of a fingerprint pattern and a technique of extracting a direction at the point.

Then, the controller 21a determines whether there exists any image division method that has not been loaded into the controller 21a among the image division methods stored in the image-division-method dictionary 22 (step B5). When determining that there exists any image division method that has not been loaded into the controller 21a (YES in step B5), the controller 21a repeatedly executes the processing from steps B2 to B4 until all the image division methods are loaded therein. On the other hand, when determining that there exists no image division method that has not been loaded into the controller 21a (NO in step B5), the controller 21a supplies, to the feature integration section 25a, feature data corresponding to the respective image division methods which are extracted by the feature extraction section 24a.

Then, the feature integration section 25a integrates the feature data corresponding to the respective image division methods which are extracted by the feature extraction section 24a into one feature data and supplies, to the controller 21a, the integrated feature data as a processing result (step B6). In this feature integration processing, the feature integration section 25a applies matching processing to the plurality of feature data extracted by the feature extraction section 24a and uses the average value of the positions or directions of feature points associated with each other as new feature data to construct the entire feature data after integration. This matching processing itself can be realized by a conventional technique and is disclosed in, e.g., JP 59-142676.

Finally, the controller 21a supplies, to the result output section 3a, the integrated feature data supplied from the feature integration section 25a (step B7). The output unit mentioned here may be a display unit such as a display in the usage where an operator checks the feature data extracted from the fingerprint image. When the integrated feature data is displayed in a superimposed manner on original input fingerprint image data on a display or the like, an operator can perform check processing more easily. Further, the plurality of feature data may directly be output to an output unit such as a display without being integrated into one feature data for quality check.

Therefore, according to the present exemplary embodiment, by previously storing a plurality of image division methods, processing input image data for respective image division methods, and integrating feature extraction results corresponding to respective image division methods into one feature data, instability in the feature extraction results, which is caused depending on the image division method, can be reduced to thereby provide stable feature extraction processing results.

(Third Exemplary Embodiment)

A third exemplary embodiment of the present invention will be described in detail with reference to FIGS. 7 to 9.

Referring to FIG. 7, an image matching apparatus (image matching system) according to the present exemplary embodiment includes an image input section 1 that holds and supplies a fingerprint image input through a fingerprint direct input device or the like, a data processing unit 2b that operates under program control, and a result output section 3b that outputs a processing result.

The data processing unit 2b functionally includes an image-division-method dictionary 22, an image division section 23, a feature extraction section 24a, a database section 26, a matching section 27, a matching result integration section 25b, and a controller 21b.

The above respective section roughly operate as follows. The image-division-method dictionary 22, image division section 23, and feature extraction section 24a operate in the same manner as in the second exemplary embodiment, and the descriptions thereof are omitted here. The database section 26 stores feature data corresponding to respective image division methods which are extracted by the feature extraction section 24a. The matching section 27 checks matching between feature data of the fingerprint image extracted by the feature extraction section 24a and feature data corresponding to respective image division methods stored in the database section 26 and generates matching data or matching scores as matching results. The matching result integration section 25b integrates the matching results corresponding to the respective image division methods which are generated by the matching section 27. The controller 21b controls the above respective section in the data processing unit 2b. The functions of the above section are realized by a computer executing a previously set program. This program is stored in a storage medium such as a memory or a hard disk.

With reference to FIG. 7 and flowcharts of FIGS. 8 and 9, the entire operation of the present exemplary embodiment will be described in detail.

It is necessary to previously perform fingerprint registration processing in fingerprint matching for identity verification. Thus, operation at the fingerprint registration time will first be described.

Figure 8:
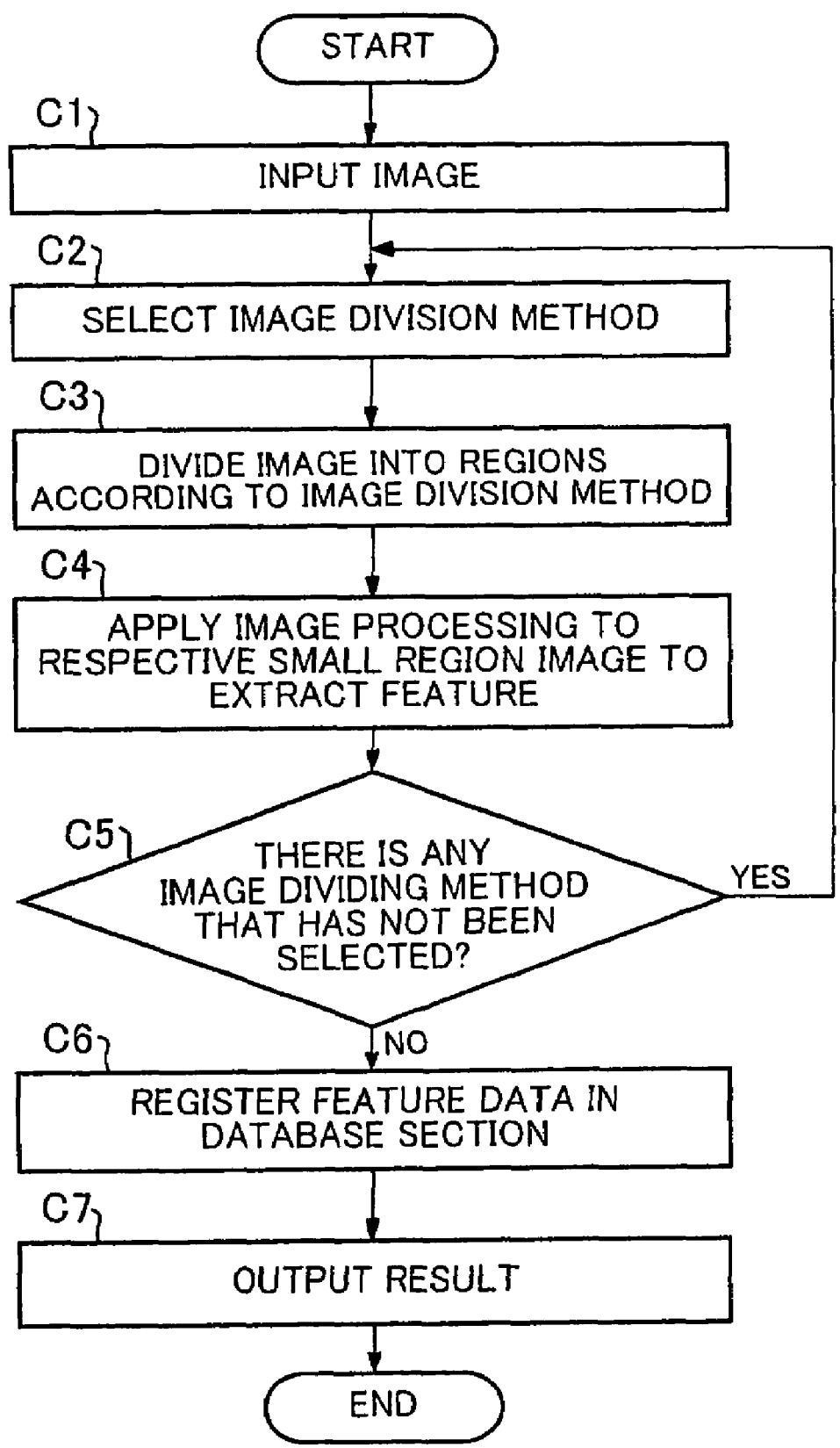
FIG. 8 is a flowchart showing operation of the image matching apparatus according to the third exemplary embodiment of the present invention at registration time.

FIG. 8 is a flowchart showing operation at the fingerprint registration time. A fingerprint image input to the image input section 1 is supplied to the controller 21b (step C1).

The controller 21b then searches the image-division-method dictionary 22 storing a plurality of image division methods, selects one image division method from image division methods that have not been selected, loads therein the selected one image division method, and supplies, to the image division section 23, the loaded image division method and fingerprint image supplied from the image input section 1 (step C2). The plurality of image division methods are the same as those in the second exemplary embodiment (see the description related to step B2), and the description thereof is omitted here.

Then, the image division section 23 divides the fingerprint image into a plurality of small regions according to the image division method supplied from the controller 21b and supplies, to the feature extraction section 24a, the obtained small region image data (step C3).

Subsequently, the feature extraction section 24a applies image processing to the respective small region image data supplied from the controller 21b to reconstruct the entire image based on the processing results, extracts a feature from the reconstructed image data, and supplies the extracted feature data to the controller 21b (step C4). The image processing, image reconstruction, and feature extraction are performed in the same manner as in the second exemplary embodiment (see the description related to step B4), and the descriptions thereof are omitted here.

Then, the controller 21b determines whether there exists any image division method that has not been loaded into the controller 21b among the image division methods stored in the image-division-method dictionary 22 (step C5). When determining that there exists any image division method that has not been loaded into the controller 21b (YES in step C5), the controller 21b repeatedly executes the processing from steps C2 to C4 until all the image division methods are loaded therein.

On the other hand, when determining that there exists no image division method that has not been loaded into the controller 21b (NO in step C5), the controller 21b registers, in the database section 26, the feature data of the fingerprint image corresponding to the respective image division methods which are extracted by the feature extraction section 24a (step C6).

Finally, the controller 21b supplies, to the result output section 3b, a registration result indicating "normal termination", "abnormal termination" or the like (step C7).

Next, operation at the matching time, in which the fingerprint has been registered, will be described.

Figure 9:
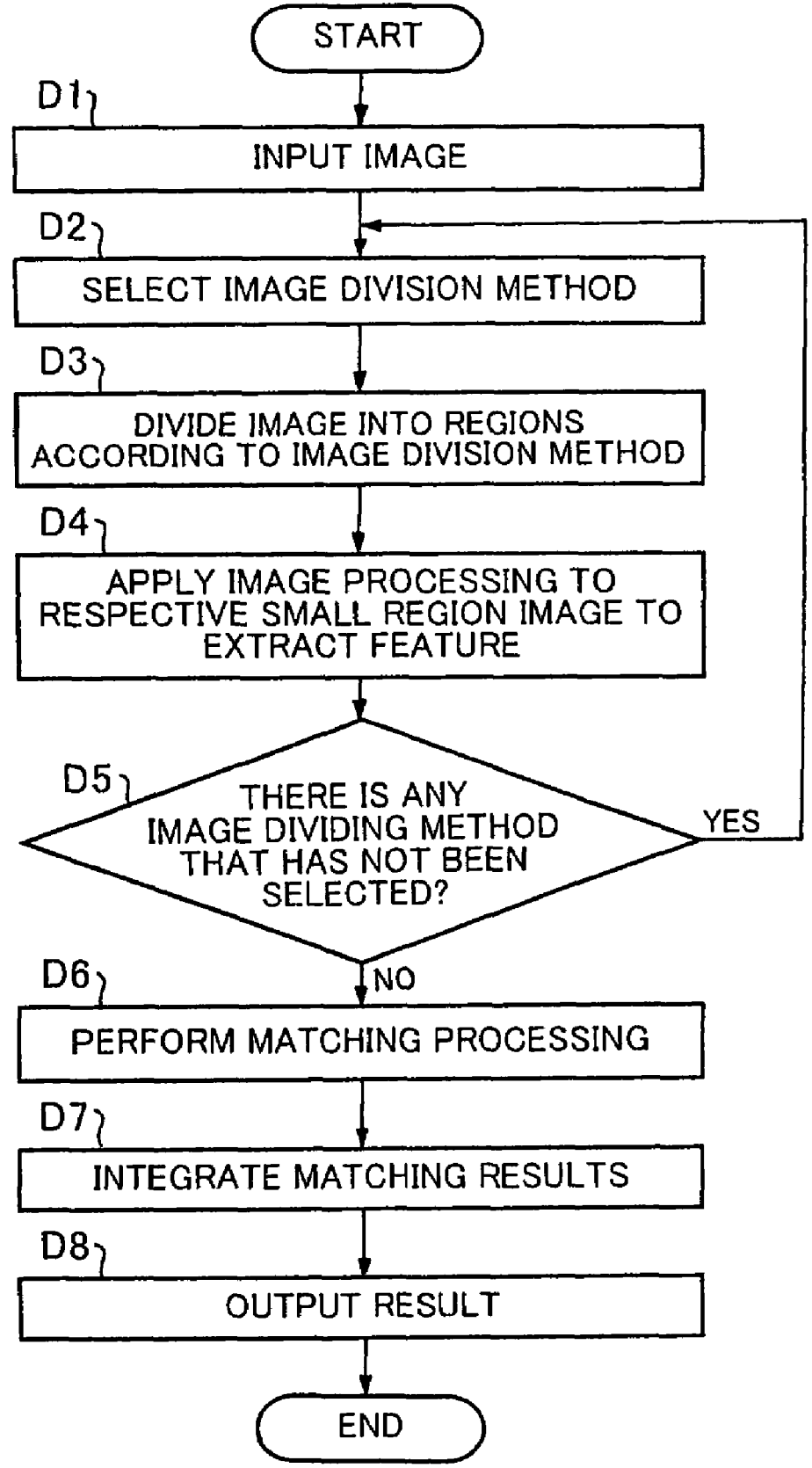
FIG. 9 is a flowchart showing operation of the image matching apparatus according to the third exemplary embodiment of the present invention at matching time.

FIG. 9 is a flowchart showing operation at the matching time. A fingerprint image input to the image input section 1 is supplied to the controller 21b (step D1).

The controller 21b then searches the image-division-method dictionary 22 storing a plurality of image division methods, selects one image division method from image division methods that have not been selected, loads therein the selected one image division method, and supplies, to the image division section 23, the loaded image division method and fingerprint image supplied from the image input section 1 (step D2). The plurality of image division methods are the same as those in the second exemplary embodiment (see the description related to step B2), and the description thereof is omitted here.

Then, the image division section 23 divides the fingerprint image into a plurality of small regions according to the image division method supplied from the controller 21b and supplies, to the feature extraction section 24a, the obtained small region image data (step D3).

Subsequently, the feature extraction section 24a applies image processing to the respective small region image data supplied from the controller 21b to reconstruct the entire image based on the processing results, extracts a feature from the reconstructed image data, and supplies the extracted feature data to the controller 21b (step D4). The image processing, image reconstruction, and feature extraction are performed in the same manner as in the second exemplary embodiment (see the description related to step B4), and the descriptions thereof are omitted here.

Then, the controller 21b determines whether there exists any image division method that has not been loaded into the controller 21b among the image division methods stored in the image-division-method dictionary 22 (step D5). When determining that there exists any image division method that has not been loaded into the controller 21b (YES in step D5), the controller 21b repeatedly executes the processing from steps D2 to D4 until all the image division methods are loaded therein.

On the other hand, when determining that there exists no image division method that has not been loaded into the controller 21b (NO in step D5), the controller 21b loads therein the feature data corresponding to the respective image division methods which are stored in the database section 26 and supplies the feature data to the matching section 27 together with feature data corresponding to the respective image division methods extracted from the input fingerprint image.

Then, the matching section 27 checks matching between the extracted feature data of the input fingerprint image and registered feature data corresponding to respective image division methods to generate matching data or matching scores and supplies the matching results to the matching result integration section 25b (step D6). Here, matching of all combinations between the plurality of feature data of the input fingerprint image and plurality of registered feature data may be checked. Alternatively, matching of only combinations between the feature data of corresponding image division method may be checked. This matching processing itself can be realized by a conventional technique and is disclosed in, e.g., JP 59-142676.

Further, the matching result integration section 25b integrates the matching data or matching scores and supplies the integrated matching data or matching score to the controller 21b (step D7). In the matching data integration processing, common corresponding feature amount in the plurality of matching data may be used as a new feature amount so as to generate the integrated matching data. In the matching score integration processing, the average value of all the matching scores may be used as a new matching score value so as to generate integrated matching score. Alternatively, the maximum value or minimum value of all the matching score may be used as a new matching score value so as to generate integrated matching score.

Finally, the controller 21b supplies the integrated matching data or matching score to the result output section 3b (step D8). Here, in the usage of personal authentication, the integrated matching score may be compared with a previously set matching score threshold to output, to the result output section 3b, a determination result indicating whether the identity of the fingerprint to be checked is valid.

Therefore, according to the present exemplary embodiment, by previously storing a plurality of image division methods, processing input image data for respective image division methods, checking matching between the extracted feature data and feature data to be compared registered in the database both of which correspond to the respective division methods, and integrating the obtained matching results, instability in the matching results, which is caused depending on the image division method, can be reduced to thereby provide stable matching results. Thus, it is possible to reduce uncertainty of the matching scores between images and identification error rate in the image matching system, thereby enhancing identification accuracy of the image matching system.

(Fourth Exemplary Embodiment)

A fourth exemplary embodiment of the present invention will be described in detail with reference to FIG. 10. The configuration (see FIG. 7) of an image matching apparatus (image matching system) according to the present exemplary embodiment and operation (see FIG. 8) thereof at the fingerprint registration time are the same as those of the third exemplary embodiment. The only different point between the third and fourth exemplary embodiments is operation at the matching time. With reference to a flowchart of FIG. 10, operation at the matching time, in which the fingerprint has been registered, will be described in detail.

FIG. 10 is a flowchart showing operation at the matching time. A fingerprint image input to the image input section 1 is supplied to the image division section 23 through the controller 21b (step E1). Then, the image division section 23 divides the fingerprint image into a plurality of small regions according to a fixed image division method and supplies, to the feature extraction section 24a, the obtained small region image data (step E2).

Subsequently, the feature extraction section 24a applies image processing to the respective small region image data supplied from the controller 21b to reconstruct the entire image based on the processing results, extracts a feature from the reconstructed image data, and supplies the extracted feature data to the controller 21b (step E3). The image processing, image reconstruction, and feature extraction are performed in the same manner as in the second exemplary embodiment (see the description related to step B4), and the descriptions thereof are omitted here.

Then, the controller 21b loads therein the feature data corresponding to respective image division methods which are registered in the database section 26 and supplies, to the matching section 27, supplied feature data of the fingerprint image and feature data corresponding to respective image division methods which are registered in the database section 26 (step E4).

Then, the matching section 27 checks matching between the feature data extracted from the fingerprint image and registered feature data corresponding to respective image division methods to generate matching results or matching scores and supplies the matching results or matching scores to the matching result integration section 25b (step E5). Here, matching between the feature data of the input fingerprint image and the plurality of feature data to be compared are performed respectively. This matching processing itself can be realized by a conventional technique and is disclosed in, e.g., JP 59-142676.

Further, the matching result integration section 25b integrates the matching results or matching scores and supplies the integrated matching result or matching score to the controller 21b (step E6). In the matching score integration processing, the average value of all the matching scores may be used as a new matching score value so as to generate integrated matching score. Alternatively, the maximum value or minimum value of all the matching score may be used as a new matching score value so as to generate integrated matching score.

Finally, the controller 21b supplies the integrated matching result or matching score to the result output section 3b (step E7).

Therefore, according to the present exemplary embodiment, the number of times of the feature extraction processing in which a large processing amount is required at the matching time can be reduced to only one, so that it is possible to realize a highly accurate fingerprint personal authentication function capable of obtaining stable matching results even in an apparatus with less computational resource, such as a mobile terminal.

Although the first to fourth exemplary embodiments of the present invention have been shown and described, the present invention is not limited to the above exemplary embodiments, and it will be apparent to those having ordinary skill in the art that a number of changes, modifications, or alternations to the invention as described herein may be made based on the description of appended claims without departing from the scope of the present invention. All such changes, modifications, and alternations should therefore be seen as within the scope of the present invention.

For example, when at least some functions of the respective section that constitute the image processing apparatus according to the first exemplary embodiment, image feature extraction apparatus according to the second exemplary embodiment, or image matching apparatus (image matching system) according to the third and fourth exemplary embodiment are realized by using program codes, the program codes and a recording medium that stores the program codes are included in the scope of the present invention. In this case, when the above functions are realized in cooperation with other software, such as an operating system or application software, the program codes of the other software are also included in the scope of the present invention.

Industrial Applicability

The present invention is useful for an image processing, image feature extraction, and image matching apparatus, method, and program, and an image matching system which are suitably used for processing a fingerprint pattern image, a palm pattern image, a muzzle pattern image, an iris pattern image, a face pattern image, a vein pattern image, and a texture pattern image.

The invention claimed is:

1. An image matching apparatus comprising:
matching means for extracting an image feature from each division region of an input image to generate feature data and performing matching between the feature data and feature data for authentication so as to generate a matching result;
control means for causing the matching means to act on the input image according to a plurality of input image division methods; and
matching integration means for integrating a plurality of matching results generated using the plurality of input image division methods to generate integrated matching data.

2. The image matching apparatus according to claim 1, wherein
the matching result is a corresponding feature between the feature data of the input image and feature data for authentication, and
the matching integration means sets a common corresponding feature amount of the plurality of matching results as the corresponding feature amount of the integrated matching data.

3. The image matching apparatus according to claim 1, wherein
at least one of the position, size, and shape of the division region is different between the plurality of input image division methods.

4. An image matching method comprising:
using an image processing apparatus to perform the steps of:
extracting an image feature from each division region of image data while changing a previously set image division method to generate a plurality of feature data;
performing matching between the plurality of feature data and externally input feature data for authentication so as to generate a plurality of matching data; and
integrating the plurality of matching data to generate integrated matching data.

5. The image matching method according to claim 4, wherein
the obtaining the plurality of feature data changes at least one of the position, size, and shape of an image division region to change the image division method.

6. An image matching system comprising:
means for extracting an image feature from each division region of image data while changing a previously set image division method to generate a plurality of feature data;
means for performing matching between the plurality of feature data and externally input feature data for authentication to obtain a plurality of matching score data;
means for integrating the plurality of matching score data to generate integrated matching score data; and
means for comparing the integrated matching score data and a previously set threshold to perform authentication.

7. The image matching system according to claim 6, wherein
the means for obtaining the plurality of feature data changes at least one of the position, size, and shape of an image division region to change the image division method.

8. The image matching system according to claim 6, wherein
the means for generating the integrated matching score data calculates at least one of the average value, maximum value, and minimum value of the plurality of matching score data to set the calculated value as the value of the integrated matching score data.

9. A non-transitory computer readable medium storing an image matching program allowing a computer to execute:
obtaining a plurality of feature data from image data by changing a previously set image division method;
performing matching between the plurality of feature data and externally input feature data for authentication to obtain a plurality of matching data; and
integrating the plurality of matching data to generate integrated matching data.

* * * * *